US008337760B2

(12) United States Patent
Wolters

(10) Patent No.: US 8,337,760 B2
(45) Date of Patent: Dec. 25, 2012

(54) RESONANT FREQUENCY BOTTLE SANITATION

(75) Inventor: Thomas S. Wolters, Algonquin, IL (US)

(73) Assignee: PepsiCo, Inc., Chicago, IL (US)

( * ) Notice: Subject to any disclaimer, the term of this patent is extended or adjusted under 35 U.S.C. 154(b) by 397 days.

(21) Appl. No.: 12/647,088

(22) Filed: Dec. 24, 2009

(65) Prior Publication Data

US 2010/0098597 A1 Apr. 22, 2010

Related U.S. Application Data

(62) Division of application No. 11/182,126, filed on Jul. 15, 2005, now Pat. No. 7,799,137.

(51) Int. Cl.

| | |
|---|---|
| ***A61L 2/00*** | (2006.01) |
| ***B06B 1/00*** | (2006.01) |
| ***B08B 5/04*** | (2006.01) |
| ***B08B 3/00*** | (2006.01) |
| ***A23N 15/00*** | (2006.01) |
| ***G01N 23/00*** | (2006.01) |

(52) U.S. Cl. ........ 422/128; 422/127; 134/125; 134/129; 134/135; 134/172; 134/198; 99/451; 99/645; 99/DIG. 12; 250/455.11; 250/492.1

(58) Field of Classification Search .................... 422/20, 422/127–128, 22, 24, 911; 134/21, 125, 134/129, 135, 172, 198, 1, 22.1, 166 R, 22.18; 99/451, 645, DIG. 12; 250/455.11, 492.1
See application file for complete search history.

(56) References Cited

U.S. PATENT DOCUMENTS

| | | | | |
|---|---|---|---|---|
| 1,977,138 | A | 10/1934 | Newey | |
| 3,208,613 | A * | 9/1965 | Brainard | 414/415 |
| 3,467,363 | A | 9/1969 | Reichel | |
| 4,201,556 | A | 5/1980 | Olsson | |
| 4,373,944 | A | 2/1983 | Glick et al. | |
| 4,461,651 | A * | 7/1984 | Hall | 134/1 |
| 5,711,327 | A | 1/1998 | Fields | |

(Continued)

FOREIGN PATENT DOCUMENTS

| | | |
|---|---|---|
| GB | 2168043 | 6/1986 |
| JP | 2002081635 | 3/2002 |

OTHER PUBLICATIONS

Braun, Simon G., et al., Encyclopedia of Vibration, vols. 1-3, pp. 1443-1479, Elsevier. 2001.

(Continued)

*Primary Examiner* — Jill Warden
*Assistant Examiner* — Monzer Chorbaji
(74) *Attorney, Agent, or Firm* — Banner & Witcoff, Ltd.

(57) ABSTRACT

A system and method of cleaning an enclosure of a container defined by inner walls, including providing a container, orienting the container so that the opening is lowermost and opens downwardly and generating resonant vibration in the container at a predetermined frequency and at an energy level sufficient to dislodge any loose solid particles from the inner walls of said container but not being of an energy level to impact the structural integrity of the container and maintaining the resonant vibration within the container enclosure for a sufficient time to dislodge all loose solid particles from the inner walls of said container. The system may include a resonant chamber in the form of a shroud and means to effectuate the method steps and may also include a sanitizing step in which the containers are further sanitized to render inactive any organic contaminants.

25 Claims, 3 Drawing Sheets

U.S. PATENT DOCUMENTS

| | | | | |
|---|---|---|---|---|
| 6,116,375 | A | 9/2000 | Lorch et al. | |
| 6,171,548 | B1 * | 1/2001 | Rose et al. | 422/20 |
| 6,710,357 | B1 | 3/2004 | Schweitzer | |
| 2002/0114484 | A1 | 8/2002 | Crisco et al. | |
| 2004/0151325 | A1 | 8/2004 | Hooley et al. | |
| 2004/0191114 | A1 | 9/2004 | Frost et al. | |

OTHER PUBLICATIONS

Rosen, Samuel, "Noise Control", Encyclopedia Americana, Grolier Online, pp. 1-4, Nov. 20, 2008.

* cited by examiner

RESONANT FREQUENCY BOTTLE SANITATION

CROSS-REFERENCE TO RELATED APPLICATIONS

This application is a divisional application of U.S. application Ser. No. 11/182,126, filed Jul. 15, 2005, now U.S. Pat. No. 7,799,137.

FIELD OF THE INVENTION

This invention relates generally to a method and a device controlling the treatment, e.g., cleaning, sterilizing, and prefilling the bottles, and more specifically to the cleaning of the interior of the bottles without the use of water or chemical solvents, such as peroxide.

BACKGROUND OF THE INVENTION

Various food and other substances subject to spoilage and/or contamination are commonly packaged in bottles in a fill-and-cap operation. Manufacturers of food products and beverages for human consumption typically package the beverage or food product. A variety of substances may be used to provide packaging for the products, including, but not limited to, plastics and glass. As a specific example, soft drinks typically are packaged in bottles formed from polyethylene terephthalate, otherwise known as "PET bottles." However, other plastics are also well known to the beverage and food packaging industries for use as containers for food and beverage products.

In certain cases, the present practice in the industry, and in particular for the packaging of soft drinks, is to rinse PET bottles with water and or a cleaning chemical composition prior to filling the bottle with a soft drink. Before being filled with a liquid food or other products, bottles or similar containers, especially those made of glass or similar materials, are usually subjected to several preliminary treatment steps, particularly to a thorough cleaning and complete sterilization. To improve the microbiological quality of filled liquid foods, it is known to sterilize the bottles with heat, prior to the filling operation, to kill any germs that may be present and that are dangerous to the food being filled in the container. These operations may introduce steam, hot water or superheated water into the bottle to be sterilized by means of a sterilization installation with spray nozzles, which installation is generally connected as a separate machine before a filling machine, or, in individual cases, is integrated into the filling machine. However, such processes may be subject to incomplete sterilization, for example, as a result of control valve failure, or insufficient pressure, and thus bactericide of the germs in the bottles may be incomplete, or in severe cases, non-operational.

As is generally known, certain products, especially microbiologically susceptible products, require heat treatment so as to achieve a sufficiently good keeping quality. In the case of some products a heat treatment of less than 100° Celsius will suffice (this is referred to as pasteurization), in the case of other products temperatures exceeding 100° Celsius must be applied so as to achieve a good keeping quality of these products. This is referred to as sterilization. Either process may be referred to herein as sanitizing of the containers.

The desire for greater purity and longer shelf life for bottled products has led others to use a sanitizer, such as peroxide ($H_2O_2$) that is sprayed on the interior of the bottle prior to filling to reduce the likelihood of product contamination or spoilage due to microorganisms. As can be readily appreciated, the effectiveness of the sanitizer depends on thorough coverage of the interior of the container by the sanitizer spray and also on the complete removal by rinsing or other means of the chemicals prior to filling. In spraying the sanitizer, several operating parameters can be varied to change the effectiveness of the spray coverage, such as the spray pattern, system operating pressure, sanitizer flow rate, temperature, sanitizer concentration, contact time, and the like, in order to increase the likelihood of complete sanitation. The final configuration of these parameters and the establishment of a complete spraying pattern of the inner surface of the bottles can reasonably assure effective sanitizer coverage. However, the use of chemicals in the sanitation process results in difficulties in cleaning of the sanitizing chemicals and also in the environmental disposal of used chemicals following the sanitizing operation.

The use of hot water or chemical disinfectants typically has not been considered suitable for rinsing PET bottles prior to filling because hot water or disinfectants could chemically or physically alter the characteristics of a PET bottle. Such alterations could render the bottles unsuitable for containing beverages, or may adversely affect the quality or taste of the beverage, or may even render the beverage unsuitable for human consumption.

Various devices and processes, not using unsuitable chemicals or excessively hot water, have been proposed for sanitizing containers such as bottles by contact with an ozonated rinse water. Ozone is highly reactive and is an effective oxidizing agent for sanitizing containers. Ozonated rinse water is preferable to untreated rinse water because it may be effective in removing microbes and other contaminants without changing the chemical or physical nature of the container. For example, Silberzahn, U.S. Pat. No. 4,409,188, proposes a device for sterilizing containers that comprises a rotatable immersion wheel for immersing the containers in a bath of ozone and water. Other devices using ozone as a sanitizing agent have also been proposed. Hughes, U.S. Pat. No. 5,106,495, proposes a portable water purification device using ozone as a treatment agent circulated by a pump through a venturi where the ozone is injected into the water, which is then returned to the tank after cleaning.

Some beverages, such as lemonades, mineral waters containing $CO_2$ or more acidic liquids, do not require hot filling, i.e., an increased temperature of the product, at the time of bottling due to their natural acidity. When this type of beverages is bottled, it is sufficient that adequate hygienic operating conditions are used so as to be able to produce containers being sterilized to remove any microbiological elements. However, if beverages containing alcohol and/or $CO_2$ are of such a nature that specific microorganisms may thrive and consequently the beverages become unfit for human consumption, additional plant equipment may be required for controlling these microorganisms, e.g. external rinsing, disinfection possibilities and sterile media.

To provide a thorough cleaning of the inside of a bottle, several methods have been used, some of them in conjunction with the sanitizing step. That is, a hot water rinse if properly directed into a bottle having a downwardly facing opening, where in a large number of bottles are being transported through a conveyor system. An example of such a cleaning arrangement is disclosed in Egger, U.S. Pat. No. 5,363,866. A jet nozzle arrangement is taught which provides an aeration and distribution of a cleaning agent at successive stations in the conveyor line.

Another consideration of those prior art methods and systems that have a fluid or jet stream that is directed into the enclosure defined by the container walls, and especially those which intrude there into by inserting a nozzle or other means of producing a jet flow into the enclosure itself, a possibility exists for introduction of extraneous matter and/or contamination into the bottle, which presently requires measures to avoid the possibility of such contamination.

Other methods for either cleaning or sanitizing containers, and more specifically, plastic bottles, are known, but all of these are similar to those prior art methods and systems described above. What is needed is a cleaning and sanitizing procedure that is efficient, effective and does not produce undesirable effluents or other residual elements, while simultaneously providing resource conservation and sustainability.

None of the prior art systems or methods known theretofore teach a non-aqueous method that does not utilize chemicals or other environmentally unfriendly methods of cleaning and/or sanitizing the inner surface of a bottle.

SUMMARY OF THE INVENTION

Accordingly, there is provided a system and method of cleaning an enclosure of a container, the enclosure being defined by inner walls, the method comprising providing a container having an enclosure of a predetermined height and a container opening at one end thereof, orienting the container so that the opening is lowermost and opens downwardly, generating resonant vibration in the container at a predetermined frequency in the air in the container enclosure, the predetermined resonance frequency being at least partially determined by the predetermined structural parameters of the container enclosure, the resonant vibration being at an energy level sufficient to dislodge any loose solid particles from the inner walls of said container but not being of an energy level to impact the structural integrity of the container and maintaining the resonant vibration within the container enclosure for a sufficient time to dislodge all loose solid particles from the inner walls of said container.

DETAILED DESCRIPTION OF THE PREFERRED EMBODIMENTS

Figure 1:
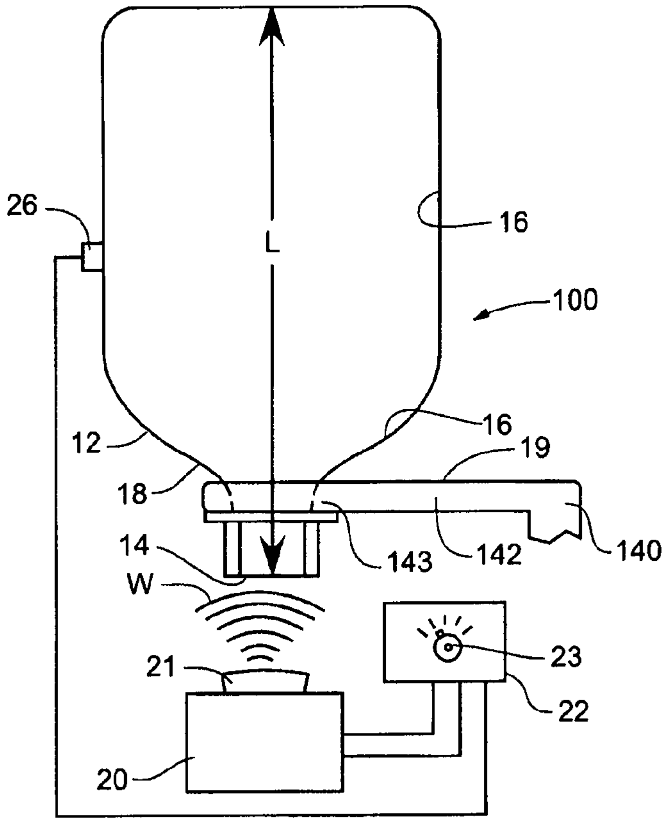
FIG. 1 is schematic view of a bottle cleaning device according to the present invention.

FIG. 1 illustrates a first embodiment of the invention, in which a bottle 12, having an opening 14, an inner wall surface 16 and a neck 18 is brought into synchronized application of an audible resonant frequency generated at a cleaning station of a bottle cleaning, sanitizing and filling system and operation. The other elements of the system and operation thereof will be discussed below with respect to FIG. 3. As shown in FIG. 1, the bottle 12 is held at the neck 18 by a brace 19 which may be a part of a conventional neck-held conveyor system, for example, that known in the art, and described in more detail below.

The cleaning station 100 includes a source 20 of an audio wave field, the source 20 being controlled by a sound pressure and frequencies processor control 22 that is capable of controlling the pitch (frequency) and volume (sound pressure level) of the audio waves generated by the source 20 through one or more external controls, one control 23 of which are shown. The volume is more accurately referred to as the sound pressure level, or SPL, of the audio waves.

The audio waves W are shown schematically as emanating from the source 20, which could be connected to a commercially available speaker, or to another audio wave generator. Preferably, the source 20 comprises a Class D Audio Amplifying Transducer, such as those commercially available as Part Nos. MAX 4295 or 4297 from Maxim Integrated Products, Inc. of Sunnyvale, Calif., as well as others being connected to one or more speakers 21. Speakers 21 may be integral with the transducer module 20, or may be separate and removed therefrom, as described below. Alternatively, the processor 22 and controls 23 may be integral with the transducer 20, the speakers 21 only being separate from the driving electronics, depending on the electronic arrangement and/or any space considerations.

The source or combination transducer 20 and speaker 21 produces audio waves at a predetermined frequency, depending on the size of the bottle and other factors, as described below. The appropriate frequency producing the greatest amount of resonance vibration may be derived from any of a number of ways, for example, by classical mode resonance, by random variance and evaluation of the resonant frequency to determine which frequency is producing the greatest amount of resonance, by theoretical calculations, or preferably, by a combination of both theoretical and observed/tested frequency response.

The theoretical method may involve a variety of methods, for example, by classical mode resonance, or by calculation based on theoretical Helmholtz resonance considerations. The frequency may be calculated to establish a Helmholtz resonance within the cavity or enclosure defined by the inner wall surface 16 of the bottle 12. That is, by creating a standing audio wave at the opening 14, as shown, the air inside of the bottle 12 is brought to its Helmholtz resonant frequency and causes the air inside the enclosed cavity of the bottle 12 to vibrate at the Helmholtz frequency, thereby also causing the inner wall surface 16 of the bottle 12 to vibrate. This vibration causes any solid particulates that may reside in the bottle to be dislodged and to fall out of the bottle, which is preferably inverted with the opening 14 facing downwardly, as shown.

The appropriate theoretical frequency for providing the desired Helmholtz resonant frequency vibration is desired from the Helmholtz equation $\omega_0=c\sqrt{(A/VL)}$ where $\omega_0$ is the desired resonant frequency;

c is the speed of sound in the ambient environment;

A is the cross-sectional area of the neck or opening 14;

V is the volume of air in the bottle 12 up to the effective opening; and

L is the effective length of the cavity from the "bottom" of the inner wall to the effective opening of the bottle 12, as shown in FIG. 1.

Thus, the theoretical frequency settings for source 20 can be easily calculated for different desired size bottles. Unfortunately, the theoretical calculations provide accurate frequency calculations for containers having relatively immovable walls, and do not take into account walls that also may vibrate at the resonant frequency. Alternatively, or in conjunction with theoretical calculations, the frequency may be adjustable in analog increments through the controls 23, and the source frequency can be calibrated within an expected range, to account for slight differences in the ambient conditions in which the bottle cleaning will take place.

According to classical mode resonance, the most effective frequency, i.e., that frequency that produces the highest amount of resonance in the bottle wall, may be very different from the frequencies that derive from Helmholtz resonance frequency calculations. That is, the Helmholtz equations are accurate for a container having rigid walls. A bottle, for example, a plastic bottle of thickness on the order of 0.010 inches, has bottle side walls that themselves vibrate, and so create a different frequency environment for the air within the bottle 12. Thus, one or more narrow frequency bands may be theoretically established for any of the different size bottles for which this system is intended, followed up by observational techniques, for example, by field monitoring of the actual vibration of a bottle wall by a transducer, such as tape accelerometer 26, that may be electrically connected to the controller 22, as shown.

Figure 2:
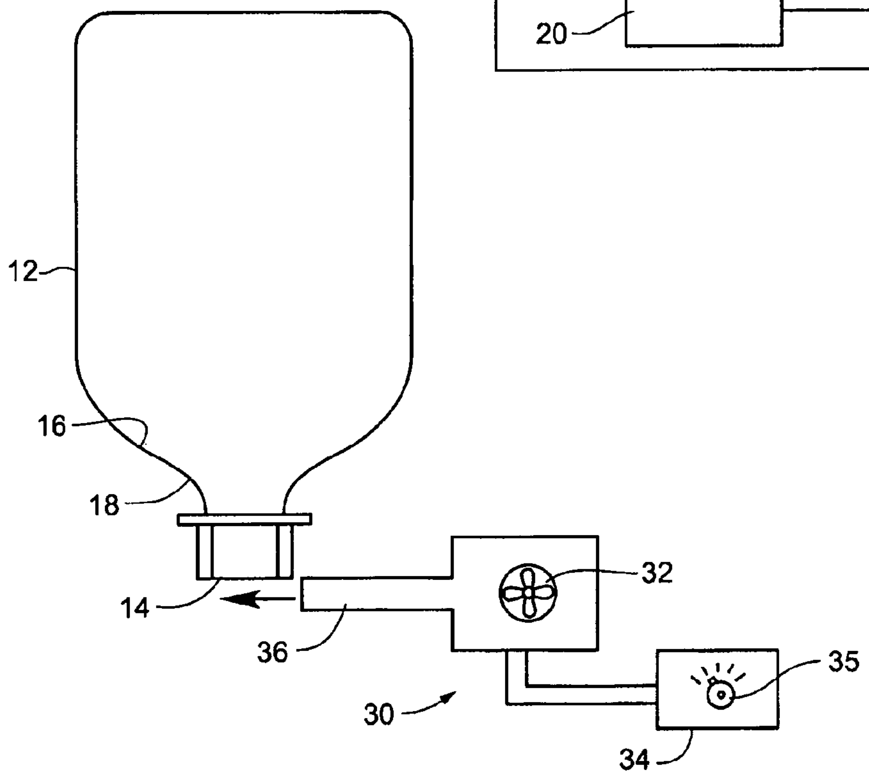
FIG. 2 illustrates an alternative embodiment of a bottle cleaning device according to the present invention.
Figure 3:
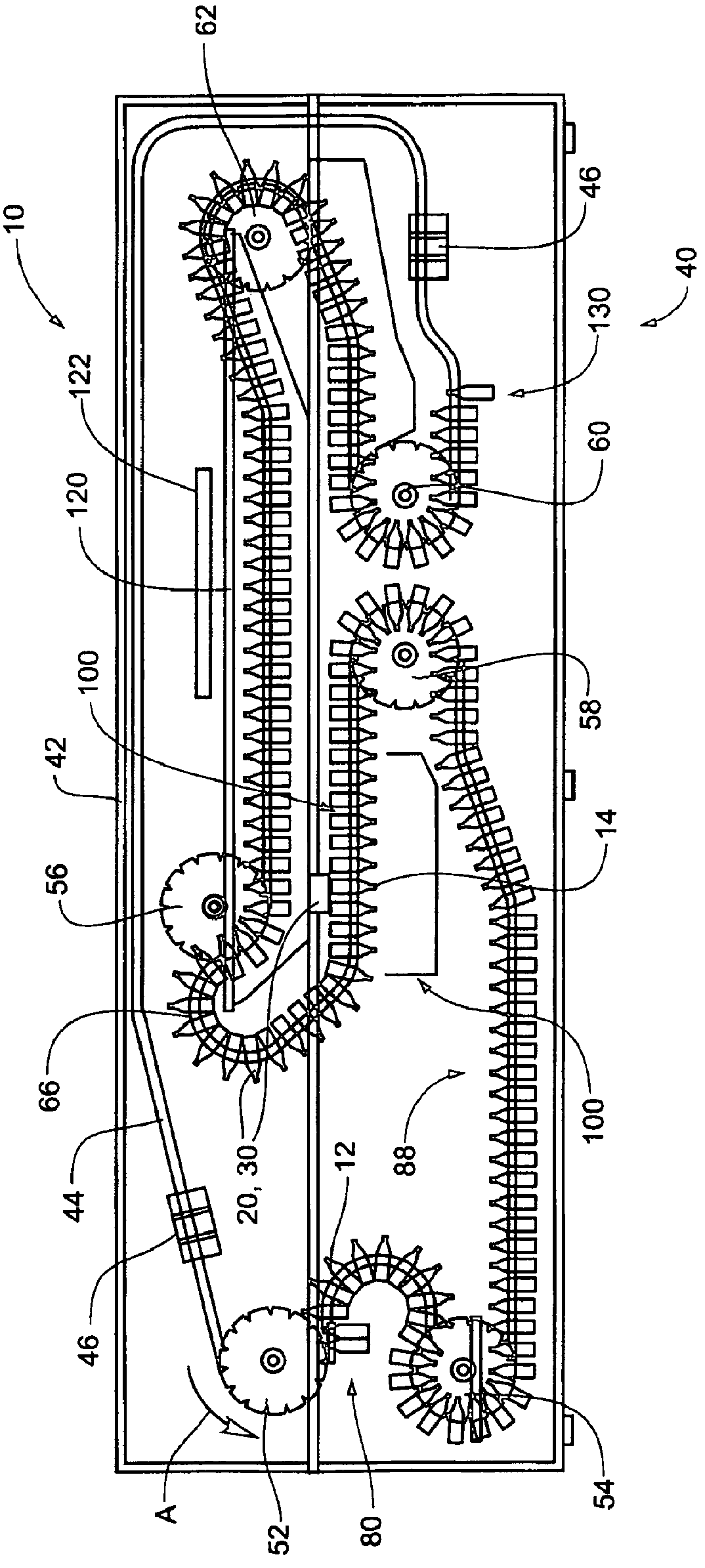
FIG. 3 is a schematic view of a system for cleaning and sanitizing containers according to the present invention.

Referring now to FIG. 2, an alternative embodiment of some of the sections of an alternative system 10' according to the invention, described in greater detail below with reference to FIG. 3, is schematically shown. FIG. 2 is a schematic representation of a bottle 12 shown in an inverted position, the bottles 12 having been oriented in an orientation in which the openings 14 are lowermost and the openings 14 are downwardly facing, as in the embodiment of FIG. 1. The embodiments shown in FIGS. 1 and 2 are essentially identical except for the generator of the resonator frequency audio wave. That is, the bottle 12 and other elements described below, for example, the bottle holding mechanism, i.e., brace 19, the transport belt, etc., can be the same as that for the FIG. 1 embodiment. Thus, where there are identical elements shown between the various views, identical reference numerals will be used.

At the cleaning station, the bottles 12 are each subjected to a passing stream of compressible fluid, such as air, that is provided by a fan 32 or other air stream generating means 30, and which directs the air stream through a conduit 36 and laterally across the opening 14 of each bottle 12. The passing air stream, depending on its intensity and velocity as calculated or derived from testing, will create a Helmholtz resonant effect on the air in the bottle 12 in accordance with the known theoretical axioms, discussed in part above. The exact characteristics of the air stream, shown by the arrow, and of the operation of the air stream generator 30 may be controlled by a controller 34, that may include one or more controls 35 to control the operation of the fan 32 or possible other parameters, for example, the diameter, orientation or opening size of the conduit 36, each of which parameters may require modifications in the resonant frequency due to change the characteristics of the air stream, as shown by the arrow. Depending on the parameters, the amount and sound pressure level of the Helmholtz resonance generated in each bottle 12 may be adjusted to provide only so much energy to dislodge any loose solid particles, while simultaneously not irreversibly alter or affect the shape of the bottles 12.

In conjunction with either of the above-described embodiments, as shown in FIGS. 1 and 2, the cleaning method may also utilize a stream of ionized air (not shown) to bathe the outside surface of the bottles 12 and thus to repel statically charged particles that may adhere to the outer surface thereof. Additionally, another mechanism may be provided for attenuation or elimination of the sound waves generated by the Helmholtz resonator or the vibration of the air in the bottles 12, which will be described in greater detail below. That is, one or more in a series of audible wave generators may be disposed in the vicinity of the bottles 12 or the bottle cleaning station, to generate an audible wave of an appropriate frequency and sound pressure level to attenuate the audio waves generated at the known Helmholtz frequency. This procedure can effectively cancel out the sound energy that escapes from the immediate vicinity of the bottle cleaning station.

The audible wave generators may be the same as that providing the initial Helmholtz frequency generator, but the audible waves are essentially 180° out of phase from the sound having the same frequency emanating from the cleaning station, thus providing an opposite wave front that effectively cancels out the sound wave energy. Ideally, these audible wave generators are disposed between the bottle cleaning station and the expected normal operating position of an operator of the system 10 and/or any anticipated bystander or observer. In this way, the operator is not subjected to the continual bandpass noise of the system, and the Helmholtz frequency audible waves are directed only in the direction of the bottle opening so as to affect the resonant cavity in each bottle only, without generally broadcasting the audible wave throughout the bottling plant, thereby minimizing or avoiding elevated ambient noise levels and any annoyance to the operator and other employees and/or passersby.

The method of cleaning the bottles 12, whether using the embodiment of FIG. 1 or of FIG. 2, requires certain standardized parameters in order to ensure the cleaning operation is complete. For example, although the Helmholtz frequency for the audible acoustic wave is one of generally well known characteristics, as calculated by the parameters of the bottle, the sound pressure level of the wave form generated by the audible wave generator 20 (FIG. 1) should be maintained within a certain range, for example, between 70 and 115 dB, so that the vibration of the bottle walls is sufficient to dislodge the loose particles, but not so intense as to destroy the structural integrity of the bottle 12. More specifically, the sound pressure level range may be maintained at between 80 and 85 dB, to produce the desired cleaning, if the bottles are in the sound field for a sufficient amount of time.

Plastic bottles, made in accordance with known bottle manufacturing techniques, have walls which are capable of becoming very thin, the thickness of some plastic bottles being reduced to as little as 0.010 inch (0.254 mm). Moreover, to retain the safety and efficacy of the cleaning operation, the times of subjecting the bottles 12 to the audible wave resonant frequency also have been established, and generally are considered to be best in a range of from about 1.0 seconds to about 3-4 seconds, based on specific bottle characteristics and the level of Helmholtz mode resonance present.

Preferably, the sound pressure level of the audible wave is about 105 dB for a preferable time of about 2.0 secs., but these parameters may vary for each bottle size. The bottle parameters may require adjustment of the audible waves, depending on a number of factors, such as ambient conditions, changes in bottle characteristics, e.g., wall thickness, bottle size, etc.

Referring now to FIG. 3, a schematic, elevational view is shown of a cleaning and sanitizing system 10 for containers, and more specifically, for bottles used to contain soft drinks of the type generally available in sizes of ½ liter, 16 and 20 ozs., 1½ liter and 2 liters. The system 10 preferably includes a frame 42, preferably comprising tubing, and has an endless chain or belt 44 for transporting bottles in the machine in the direction of the arrow A. The belt 44 is disposed over the whole length of the system and is provided with bottle holders 46, as shown. For the sake of simplicity, only a few of the bottles 12 are shown in place on the endless belt 44 in FIG. 3. The endless belt 44 is driven and operated by a plurality of wheels 52-62 and the belt is guided by a plurality of guides 66. The system shown may be any alternative embodiment of the above-described neck-held bottle conveyor system, and further described in more detail below.

The system 10 shown in FIG. 3 presents a more elaborate arrangement than one that might be shown to provide a more complete understanding of the invention. The schematic illustration of FIG. 3 shows a number of stations in the bottle handling facility presented by the system 10. For example, system 10 includes a bottle loading station 80 where fully formed empty bottles 12 are loaded on to the carriers or holders 46, from which bottles ready for filling or filled bottles have been earlier removed, as will be described below.

The bottles 12 may be initially processed in accordance with standard operating procedures, which are known in the industry, for example, testing of the wall thickness of the bottles at a station 88, as shown, or the bottles 12 may be finished in a known process that is not germane to the invention herein, and need not be further discussed.

Following the processing at station 88, the bottles 12 are brought to the bottle cleaning station 100, configured in accordance with an alternative embodiment of the present invention and as shown in FIGS. 1 and 2, described above, or a variant thereof. The bottle cleaning station 100 may be configured as shown in FIG. 1 or 2, or any other bottle cleaning station in accordance with the teachings of the present invention, or in accordance with the preferred bottle cleaning system described below in greater detail with reference to FIG. 4. As shown, the wheel 58 inverts the position of the belt 44 and the bottles 12, so that the openings 14 are all downwardly facing, as shown. The operation of the bottle cleaning station 100 is then performed on each bottle 12, as it passes through the bottle cleaning station 100, in accordance with the description of FIG. 1 or 2 above. It should be understood that the neck-held bottle arrangement as shown in FIG. 1 is preferred. However, the embodiment of system 100 schematically shows the bottles 12 being held around a central body portion, which while not preferable, is another alternative arrangement that may be feasible for purposes of the invention. Also, while the audible wave generators 20,30 are shown at the bottle cleaning station 100 directing sound wave energy from behind the bottles, the preferred method is to direct the energy into the bottle opening 14 as shown in FIGS. 1 and 4.

Following the operational procedures at the bottle cleaning station 100, the bottles are again inverted by wheel 56 to a position in which the openings are upwardly facing and the bottles are transported by the belt 44 to a bottle sanitizing station 120. At the sanitizing station 120, the bottles 12 may be illuminated by ultraviolet (UV) light 122 of an appropriate frequency, which UV light acts as a bactericide to sanitize both the outer and inner (16) surfaces of the bottle 12. Although a single UV light source 122 is shown, it is contemplated that several sources (not shown) in addition to UV light source 122 may be used, so as to provide a thorough illumination of all surfaces. Alternatively, sanitation may be performed by a standard hydroxide rinse, or by dry air blowing method, using compressed air sanitation techniques contemplated for a separate and independent invention described and claimed in a commonly assigned application to be filed later.

Following the sanitation procedures at the sanitizing station 120, the bottles 12 are transported to a bottle disengagement station 130 where the bottles 12 may be removed from the holders or carriers 46, and the carriers 46 are transported again to the bottle loading station 80 for continuing the cycle. In the meantime, the clean and sanitized bottles 12 are transported from the bottle disengagement station 130 to a standard bottle filling station (not shown), where the liquid refreshment to be contained in the bottles 12 is dispensed into the bottles 12, which bottles are then capped and packed for shipment. Alternatively, the bottle 12 may be filled at one or more stations of the system 10, the bottle filling station not being shown, but being incorporated in the system at an appropriate position.

Figure 4:
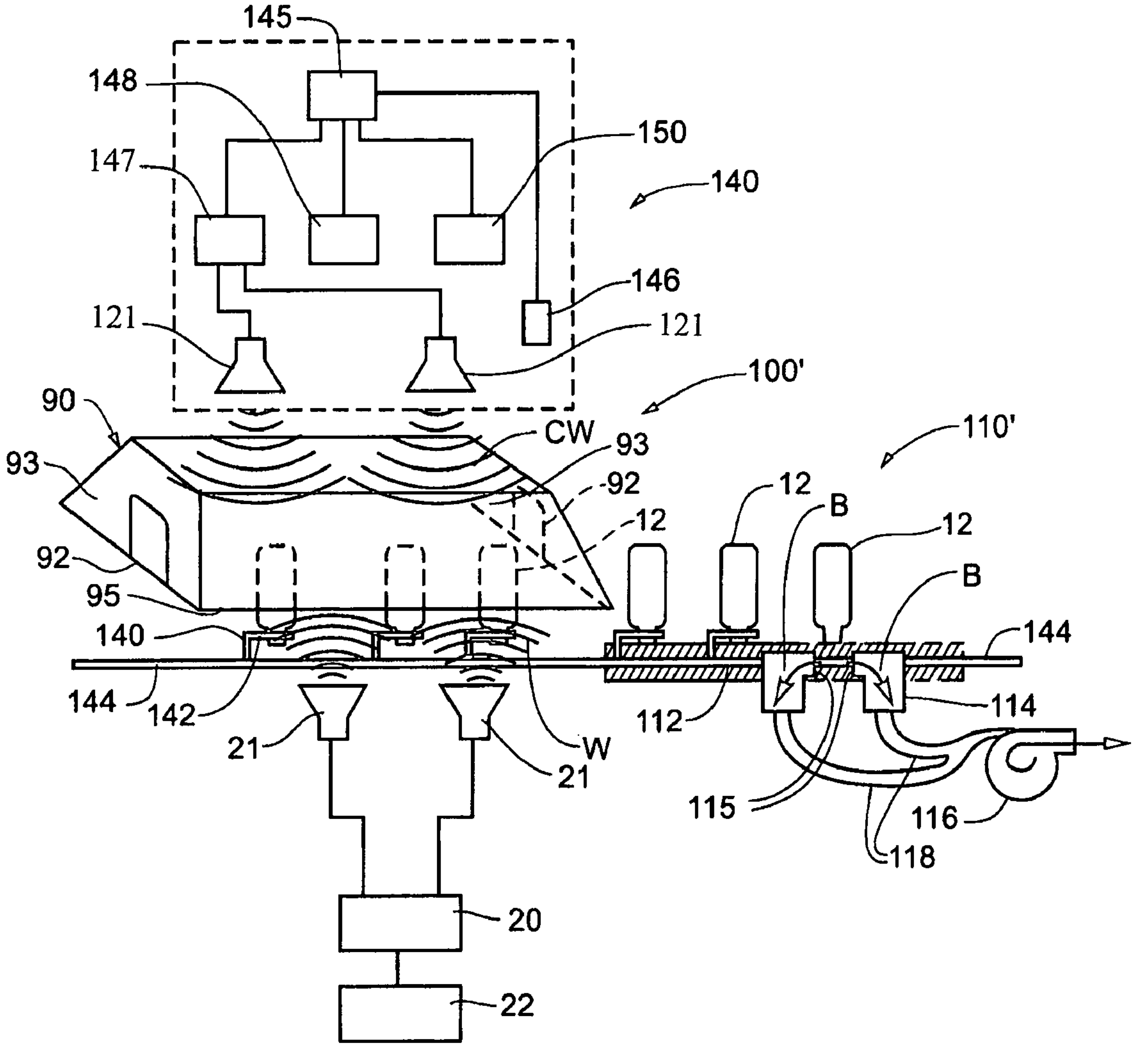
FIG. 4 is a perspective representational view of a segment of a system including an alternative embodiment of the container cleaning device.

FIG. 4 illustrates a preferred arrangement for holding containers, for example, bottles at the neck, where the containers are in an inverted, neck-down position, as shown. The feature of the invention shown in FIG. 4 may comprise the cleaning station 100' for cleaning the containers of debris, prior to passing on to a sterilization station 120 (FIG. 3). The containers are shown in FIG. 4 as being transported from one station to the next along a rail 144. The bottles 12 are retained to be conveyed along the rail 144 by a plurality of braces 19, one of which is partially shown in FIG. 1.

Braces 19 preferably comprise a rail portion 140 that is retained by the rail and slides along or with the rail 144, and which extends partially in a direction normal to the longitudinal direction of the rail 144. A second bottle holding portion 142 extends along the direction of travel of the rail, or alternatively also normally thereto, and has a constricting aperture 143 (shown in phantom in FIG. 1) for releasably holding the neck 18 of each bottle 12. As shown in FIG. 4, the bottles 12 are oriented in an inverted position when being conveyed through the bottle cleaning station 100'.

One important feature shown in the embodiment of cleaning station 100' is a resonant chamber 90, that is provided for containing and concentrating the audible sound wave energy at the cleaning station 100'. The resonant chamber 90 is shown in a partially truncated pyramidal shape, having a base side, that is, the wider portion of the truncated pyramidal resonant chamber 90, opens toward the rail 144 and the bottles 12 (shown partially in phantom) being conveyed through the cleaning station 100'. The chamber 90 acts as a shroud over the bottles 12 and includes two openings 92, one providing to the bottles 12 ingress into, and the other for egress out of, the chamber. The openings 92 have a shape and orientation to permit the passage therethrough of bottles having a variety of sizes, and the openings 92 may be made adjustable to conform with the size of the bottles being cleaned. The size of the resonant chamber 90 is preferably large enough to cover at least three bottles 12 at a time, so that depending on line speed, each bottle is within the resonant chamber 90 for a sufficient amount of time to induce sufficient modal excitation of the bottle walls 16 for purposes of dislodging any debris therefrom.

Depending on the sound pressure level, that time may be within the preferred ranges set forth above, or may be of lesser time because of the benefits of using a resonant chamber 90, including containing a major portion of the audible wave energy within the enclosure of the resonant chamber 90, concentrating and reinforcing the reflected sound waves toward the bottles by virtue of the preferably angled walls 91, of the chamber 90, and in the cancellation of the audible sound energy emanating from the bottle cleaning station 100', as will be described below.

Disposed on the opposite side of rail 144 and bottles 12 are speaker(s) 21, which are oriented to direct the audible sound energy, shown schematically by waves W emanating therefrom, towards the bottles 12 and into the resonant chamber 90. While the resonant chamber 90 is shown with five walls 93 and an open base, other configurations and arrangements are possible. For example, a second resonant chamber (not shown) may be oppositely oriented and attached to the outer base boundary 95 to enclose both the bottles 12 and the speakers 21, so as to more completely contain the audible sound wave energy within an enclosure that has only limited openings, for example, openings 92 for the bottle, and a set of second openings for passage of rail 144 therethrough. The speakers 21 are connected to a transducer 20 and control system 22, as in the embodiment shown in FIG. 1. The number and placement of speakers may be experimentally determined for the application in order to produce a uniform and adequate noise cancellation field around the chamber.

Having passed through the bottle cleaning station 100' wherein audible sound energy has loosened or dislodged any solid debris that may be in the bottle 12, gravity may suffice to cause the removal of the debris through bottle opening 14, which is directed downwardly. Optionally, and preferably, the bottles 12 are conveyed to a debris removal station 110' further along the rail 144. The debris removal station 110' may have a shroud 112 shown in partial cutaway view through which the bottle neck 18 passes, to provide a semi-enclosed space for each bottle opening 14. The shroud 112 includes therein one, or preferably more, vacuum nozzles 114 having openings 115, or a continuous vacuum rail or plenum, that are inwardly directed toward the rail 114, or toward the space where the openings 14 of each bottle 12 will pass, as shown. As the bottle openings pass the vacuum openings 115, a vacuum created by a vacuum generator 116 connected to the nozzles 114 through conduits 118, withdraws air in the direction of the arrows B from the bottle and also withdraws any entrained solid debris particulates. The air is then directed to a filter (not shown) where the debris is filtered out and the clean air is expelled to the environment. The bottles 12 in the meantime are conveyed to the next processing station, for example, a sanitizing station 120 (FIG. 3) for other appropriate processing steps to be performed thereon, before filling with product.

Another optional feature of the present invention is an audible sound energy cancellation arrangement 140, shown surrounded by a dashed line, provided adjacent to or in the vicinity of the outer walls 93 of the resonance chamber 90. Ideally the arrangement 140 is disposed between the resonance chamber 90 and the operating station which the system 10 includes for the system operator. Alternatively, or in conjunction therewith, the sound cancellation arrangement may be disposed to restrict any sound from emanating to any positions where others are in the bottling plant, so that the audible sound energy is contained within the vicinity of the bottle cleaning station 100'.

The sound cancellation arrangement 140 is shown in FIG. 4, as being surrounded by the dashed lines. The sound cancellation arrangement 140 preferably comprises one or more speakers 121 driven by one or more Class D amplifiers 147 and controlled by a central processor 145.

The controller 145 is further electrically connected to several additional elements, including an ambient noise microphone 146, a signal phase adjuster 148 and a bandpass frequency signal generator 150 that may be adjustable and have pre-set controls for certain prespecified bottles having known or calculated characteristics. Although each of these elements are shown to be electronically interconnected to a processor 145, this configuration is not required, as one or more of the elements 146, 147, 148, 150 etc., may have internal electronics that provide the necessary controlling functions and/or adjustable controls, and the elements may be connected in series to each other, (not shown) to produce the desired noise cancellation waves. Alternatively, standard ambient sound cancellation, including a complete configuration of the elements of the noise cancellation arrangement are commercially available as a stand alone modular system, and available, or example, from Silex, Inc. of Mississagua, Ontario, Canada.

In operation, sound waves (not shown) emanating from the resonance chamber 90 are sensed, both in terms of frequency and audible sound pressure level and then converted to electronic form, either analog or digital, by a transducer or converter electronics in, for example, the processor control 145. The electronic signal is then filtered by a band-pass to isolate the frequencies of interest and the signal is reprocessed in the signal phase adjuster 148 to provide an out-of-phase electrical signal that, after being passed to the Class D audio amplifier 147, is sent to be acoustically transduced into canceling sound waves CW by the speakers 121. The canceling sound waves, shown schematically as CW, are ideally essentially 180° out-of-phase from the audible sound energy emanating from the resonant chamber 90.

The frequency and sound pressure level of the sound energy coming out of the resonant chamber 90 usually emanates in an altered state because the sound energy reverberates through the resonant chamber 90 and then by vibration passes through the walls 93. Thus, calculations may be required to provide the appropriate sound pressure levels of the sound cancellation waves, CW, and synchronization of the frequency of the sound from the primary speakers 21 may be required to provide canceling sound energy waves CW needed for the proper noise cancellation technique. It has been observed that the sound waves emanating from an enclosed resonant chamber 90 are apt to drop several octaves in frequency. Thus, it is preferable that, when a resonant chamber 90 is used to concentrate the sound energy, a sound cancellation mechanism, such as arrangement 140, be utilized to reduce the ambient noise that may be audible in the environment surrounding the chamber 90. Utilizing a commercially available sound cancellation processor or algorithm provides a preferable method of automatic sensing of ambient noise frequency, phase and intensity, and also produces the required automatic calibration of the noise canceling acoustic output.

The invention herein has been described and illustrated with reference to the embodiments of FIGS. 1-4, but it should be understood that the features of the invention are susceptible to modification, alteration, changes or substitution without departing significantly from the spirit of the invention. For example, the dimensions, size and shape of the various bottles, holders, resonant chamber(s) etc. may be altered to fit specific applications. Similarly, the configuration of the bottle cleaning and sanitizing system 10, shown in FIG. 3 may be changed or modified from that shown. Accordingly, the specific embodiments illustrated and described herein are for illustrative purposes only and the invention is not limited except by the following claims and their equivalents.

I claim:

1. A system used for cleaning an enclosure of a container, the enclosure being defined by inner walls, the system comprising:

a container retainer for holding plural containers in at least one orientation relative to the horizontal, the containers having an enclosure, the enclosure having predetermined structural parameters and a container opening at one end thereof;

an orienting mechanism for orienting each container held by a belt so that the container opening is lowermost and opens downwardly;

a first shroud covering at least a bottom surface of the container;

a cleaning station for generating a resonant vibration in the container at a predetermined frequency of the air in the container enclosure, the predetermined resonance frequency being at least partially determined by the predetermined structural parameters of the container enclosure, the resonant vibration being at an energy level sufficient to dislodge any loose solid particles from the inner walls of said container but not being of an energy level to impact the structural integrity, the resonant vibration generation being performed within the first shroud, wherein the resonant vibration is maintained within the container for a sufficient time to dislodge substantially all loose solid particles from the inner walls of said container, wherein the cleaning station further comprises an audio amplifier transducer having a high acoustic output and a variable, frequency range and having a speaker directing its output toward the container opening;

a noise control cancellation arrangement that provides an out of phase acoustic wave, having similar frequency and sound pressure level as the resonant frequency generated by the audio amplifier transducer, wherein the out of phase acoustic wave is directed in a direction away from the container opening so as to essentially cancel the resonant frequency acoustic wave from emanating to the ambient environment beyond the general vicinity of the container or system; and a debris removal station, that includes a second shroud with at least one vacuum nozzle directed towards the containers.

2. The system used for cleaning an enclosure of a container according to claim 1, wherein the system further comprises a sanitizing station that sanitizes the container by irradiating the container for a sufficient period to sanitize the inner wall of any organic contaminants.

3. The system used for cleaning an enclosure of a container according to claim 2, wherein the sanitizing station directs electromagnetic rays of at least ultraviolet frequencies toward the container walls to irradiate the container.

4. The system used for cleaning an enclosure of a container according to claim 1, wherein the cleaning station further comprises an audio source configured to produce a range of audio waves at the predetermined frequency, wherein the audio source is controlled by a controller that is capable of controlling one or more of the following: pitch, frequency, volume, and sound pressure, of the sound waves.

5. The system used for cleaning an enclosure of a container according to claim 4, wherein the controller adjusts the audio wave adjacent the predetermined resonant frequency, monitors the amount of resonant vibration in the container walls, and establishes a frequency that provides the greatest amount of resonant vibration.

6. The system used for cleaning an enclosure of a container according to claim 1, wherein the cleaning station further comprises an amplified speaker capable of generating a range of frequencies and sound pressure levels so as to produce Helmholz resonance vibration in the container enclosure, the resonant vibration being at an energy level sufficient to dislodge any loose solid particles from the inner walls of said container but not being of an energy level to impact the structural integrity of the walls of the container.

7. The system used for cleaning an enclosure of a container according to claim 1, wherein the cleaning station further comprises a means for generating an air stream, which directs the air stream laterally across the container opening at a speed and energy level sufficient to generate a resonant vibration of the energy level necessary to dislodge the loose solid particles on the inner wall of the container.

8. The system used for cleaning an enclosure of a container according to claim 7, wherein the cleaning station further comprises a noise control retention mechanism that provides an out of phase acoustic wave, having the identical frequency and intensity as the resonant vibration generated by the stream of compressible fluid, wherein the out of phase wave is directed in a direction away from the container opening so as to essentially cancel the resonant frequency wave from emanating to the ambient environment beyond the vicinity of the container.

9. The system used for cleaning an enclosure of a container according to claim 1, wherein the cleaning station generates an audio wave of an intensity in a range of from approximately 70 dB to approximately 115 dB.

10. The system used for cleaning an enclosure of a container according to claim 1, wherein the cleaning station generates an audio wave of an intensity in a range of from approximately 90 dB to approximately 115 dB for a period of from approximately 2.0 seconds to approximately 3.0 seconds.

11. A system used for cleaning an enclosure of a container, the enclosure being defined by inner walls, the system comprising:

an assembly for holding a plurality of containers, wherein the containers are in an inverted, neck-down position, the containers having an enclosure, the enclosure having predetermined structural parameters and a container opening at one end thereof;

a source of an audio wave, the source comprising a transducer module and at least one speaker directed towards the source of the bottle opening, wherein the source of the audio wave generates a resonant vibration in the bottle at a predetermined frequency of the air in the enclosure, the predetermined frequency being at least partially determined by the predetermined structural parameters of the enclosure, the resonant vibration being at an energy level sufficient to dislodge any loose solid particles from the inner walls of said bottle but not being of an energy level to impact the structural integrity;

a controller that is capable of controlling one or more of the following: pitch, frequency, volume, and sound pressure, of the audio waves, wherein the controller adjusts the audio wave, monitors the amount of resonant vibration in the container walls, and establishes a frequency that provides the greatest amount of resonant vibration;

a resonant chamber that includes a first opening providing to the containers ingress into the resonant chamber and a second opening proving to the container egress out of the resonant chamber, wherein the containers are maintained within the resonant chamber for a sufficient time to dislodge substantially all loose solid particles from the inner walls of said container;

a noise control cancellation arrangement that provides an out of phase acoustic wave, having similar frequency and sound pressure level as the resonant frequency generated by the audio amplifier transducer, wherein the out of phase acoustic wave is directed in a direction away from the container opening so as to essentially cancel the resonant frequency acoustic wave from emanating to the ambient environment beyond the general vicinity of the container or system; and a sanitizing station that sanitizes the container by irradiating the container for a sufficient period to sanitize the inner wall of any organic contaminants, wherein the sanitizing station directs electromagnetic rays of at least ultraviolet frequencies toward the container walls to irradiate the container.

12. The system used for cleaning an enclosure of a container according to claim 11, wherein the at least one speaker is capable of generating a range of frequencies and sound pressure levels so as to produce Helmholz resonance vibration in the container enclosure, the resonant vibration being at an energy level sufficient to dislodge any loose solid particles from the inner walls of said container but not being of an energy level to impact the structural integrity of the walls of the container.

13. The system used for cleaning an enclosure of a container according to claim 11, further including a debris removal station that includes a shroud with at least one vacuum nozzle directed towards the container.

14. The system used for cleaning an enclosure of a container according to claim 11, wherein the audio wave is of an intensity in a range of from approximately 70 dB to approximately 115 dB.

15. The system used for cleaning an enclosure of a container according to claim 11, wherein the audio wave is of an intensity in a range of from approximately 90 dB to approximately 115 dB for a period of from approximately 2.0 seconds to approximately 3.0 seconds.

16. A system used for cleaning an enclosure of a container, the enclosure being defined by inner walls, the system comprising:

a container retainer for holding plural containers in at least one orientation relative to the horizontal, the containers having an enclosure, the enclosure having predetermined structural parameters and a container opening at one end thereof;

an orienting mechanism for orienting each container held by a belt so that the container opening is lowermost and opens downwardly;

a first shroud covering at least a bottom surface of the container;

a cleaning station for generating a resonant vibration in the container at a predetermined frequency of the air in the container enclosure, the predetermined resonance frequency being at least partially determined by the predetermined structural parameters of the container enclosure, the resonant vibration being at an energy level sufficient to dislodge any loose solid particles from the inner walls of said container but not being of an energy level to impact the structural integrity, the resonant vibration generation being performed within the first shroud, wherein the resonant vibration is maintained within the container for a sufficient time to dislodge substantially all loose solid particles from the inner walls of said container, wherein the cleaning station further comprises a means for generating an air stream, which directs the air stream laterally across the container opening at a speed and energy level sufficient to generate a resonant vibration of the energy level necessary to dislodge the loose solid particles on the inner wall of the container, and wherein the cleaning station further comprises a noise control retention mechanism that provides an out of phase acoustic wave, having the identical frequency and intensity as the resonant vibration generated by the air stream, wherein the out of phase wave is directed in a direction away from the container opening so as to essentially cancel the resonant frequency wave from emanating to the ambient environment beyond the vicinity of the container; and a debris removal station, that includes a second shroud with at least one vacuum nozzle directed towards the containers.

17. The system used for cleaning an enclosure of a container according to claim 16, wherein the system further comprises a sanitizing station that sanitizes the container by irradiating the container for a sufficient period to sanitize the inner wall of any organic contaminants.

18. The system used for cleaning an enclosure of a container according to claim 17, wherein the sanitizing station directs electromagnetic rays of at least ultraviolet frequencies toward the container walls to irradiate the container.

19. The system used for cleaning an enclosure of a container according to claim 16, wherein the cleaning station further comprises an audio source configured to produce a range of audio waves at the predetermined frequency, wherein the audio source is controlled by a controller that is capable of controlling one or more of the following: pitch, frequency, volume, and sound pressure, of the sound waves.

20. The system used for cleaning an enclosure of a container according to claim 19, wherein the controller adjusts the audio wave adjacent the predetermined resonant frequency, monitors the amount of resonant vibration in the container walls, and establishes a frequency that provides the greatest amount of resonant vibration.

21. The system used for cleaning an enclosure of a container according to claim 16, wherein the cleaning station further comprises an amplified speaker capable of generating a range of frequencies and sound pressure levels so as to produce Helmholz resonance vibration in the container enclosure, the resonant vibration being at an energy level sufficient to dislodge any loose solid particles from the inner walls of said container but not being of an energy level to impact the structural integrity of the walls of the container.

22. The system used for cleaning an enclosure of a container according to claim 16, wherein the cleaning station further comprises an audio amplifier transducer having a high acoustic output and a variable, frequency range and having a speaker directing its output toward the container opening.

23. The system used for cleaning an enclosure of a container according to claim 22, further comprising a noise control cancellation arrangement that provides an out of phase acoustic wave, having similar frequency and sound pressure level as the resonant frequency generated by the audio amplifier transducer, wherein the out of phase acoustic wave is directed in a direction away from the container opening so as to essentially cancel the resonant frequency acoustic wave from emanating to the ambient environment beyond the general vicinity of the container or system.

24. The system used for cleaning an enclosure of a container according to claim 16, wherein the cleaning station generates an audio wave of an intensity in a range of from approximately 70 dB to approximately 115 dB.

25. The system used for cleaning an enclosure of a container according to claim 16, wherein the cleaning station generates an audio wave of an intensity in a range of from approximately 90 dB to approximately 115 dB for a period of from approximately 2.0 seconds to approximately 3.0 seconds.

* * * * *